(12) United States Patent
Fowler et al.

(10) Patent No.: US 9,827,052 B2
(45) Date of Patent: Nov. 28, 2017

(54) TWO-PART TRACKING REFERENCE STRUCTURE

(71) Applicant: Brainlab AG, Munich (DE)

(72) Inventors: Maria Fowler, Munich (DE); Norman Plassky, Erfurt (DE)

(73) Assignee: Brainlab AG, Munich (DE)

( * ) Notice: Subject to any disclaimer, the term of this patent is extended or adjusted under 35 U.S.C. 154(b) by 218 days.

(21) Appl. No.: 14/440,387

(22) PCT Filed: Nov. 4, 2013

(86) PCT No.: PCT/EP2013/072928
§ 371 (c)(1),
(2) Date: May 4, 2015

(87) PCT Pub. No.: WO2014/072251
PCT Pub. Date: May 15, 2014

(65) Prior Publication Data
US 2015/0297314 A1    Oct. 22, 2015

(30) Foreign Application Priority Data

Nov. 6, 2012   (WO) ................. PCT/EP2012/071931

(51) Int. Cl.
*A61B 5/05* (2006.01)
*A61B 19/08* (2006.01)
(Continued)

(52) U.S. Cl.
CPC ............ *A61B 19/54* (2013.01); *A61B 5/0059* (2013.01); *A61B 5/055* (2013.01); *A61B 5/062* (2013.01);
(Continued)

(58) Field of Classification Search
None
See application file for complete search history.

(56) References Cited

U.S. PATENT DOCUMENTS 5,651,771 A    7/1997  Tangherlini et al.
6,451,027 B1 *  9/2002  Cooper .............. A61B 1/00149
                                          606/130
(Continued)

FOREIGN PATENT DOCUMENTS

DE        19639615 A1      4/1998
DE    WO2011/038759    *   4/2011
(Continued)

OTHER PUBLICATIONS

International Search Report and Written Opinion for International Application No. PCT/EP2013/072928 dated May 28, 2014 (5 pages).

(Continued)

*Primary Examiner* — Patricia Park
(74) *Attorney, Agent, or Firm* — Tucker Ellis LLP.

(57) ABSTRACT

The present invention relates to a tracking reference structure for localizing and tracking an object by means of a medical tracking system, said structure comprising: —a first part (1) which forms a support structure for at least one tracking marker (3); and—a second part (2) which is configured to be fixed to said object, wherein a positionally fixed connection between the first part (1) and the second part (2) is established by means of an interface comprising at least one resiliently articulated element (4) on the first part (1) and/or second part (2), which engage(s) with the respective other part (2, 1), and wherein the resiliently articulated element (4) is configured such that its restoring spring force alone is already sufficient to positionally fix the connection. The present invention also relates to a tracking reference system comprising such a tracking reference structure which in turn comprises at least one first part (1), wherein any additional first part(s) (1) support(s) a different type of tracking marker (3) and said different first parts (1) can be interchangeably connected to the second part (2), and (Continued)

wherein the tracking markers (3) of each of said different first parts (1) are in particular placed in the same spatial position when being coupled to the second part (2).

17 Claims, 6 Drawing Sheets

(51) Int. Cl.
    *A61B 19/00*     (2006.01)
    *F16B 2/18*     (2006.01)
    *A61B 46/00*     (2016.01)
    *A61B 5/00*     (2006.01)
    *A61B 5/055*     (2006.01)
    *A61B 5/06*     (2006.01)
    *A61B 6/03*     (2006.01)
    *A61B 8/08*     (2006.01)
    *A61B 17/00*     (2006.01)
    *A61B 90/00*     (2016.01)
    *A61B 34/20*     (2016.01)

(52) U.S. Cl.
    CPC ............. *A61B 6/032* (2013.01); *A61B 8/481* (2013.01); *A61B 46/00* (2016.02); *A61B 90/39* (2016.02); *F16B 2/185* (2013.01); *A61B 2017/00477* (2013.01); *A61B 2017/00862* (2013.01); *A61B 2034/2055* (2016.02); *A61B 2090/397* (2016.02); *A61B 2090/3925* (2016.02); *A61B 2090/3937* (2016.02); *A61B 2090/3954* (2016.02); *A61B 2090/3966* (2016.02); *A61B 2090/3979* (2016.02); *A61B 2090/3983* (2016.02); *A61B 2090/3991* (2016.02)

(56) References Cited

U.S. PATENT DOCUMENTS

| | | | | |
|---|---|---|---|---|
| 2002/0133058 | A1* | 9/2002 | Calderwood | A61B 1/00142 600/122 |
| 2007/0232897 | A1* | 10/2007 | Horndler | A61B 6/032 600/424 |
| 2008/0167553 | A1* | 7/2008 | Paltieli | A61B 5/061 600/437 |
| 2011/0071389 | A1 | 3/2011 | Simon et al. | |
| 2011/0166446 | A1* | 7/2011 | Whitmore, III | A61B 19/54 600/426 |
| 2012/0184839 | A1* | 7/2012 | Woerlein | A61B 19/54 600/407 |
| 2012/0248692 | A1* | 10/2012 | Uchida | B65H 1/266 271/264 |
| 2013/0167847 | A1* | 7/2013 | Rogers | A61B 19/081 128/869 |
| 2013/0317358 | A1* | 11/2013 | Karasz | A61B 5/064 600/424 |

FOREIGN PATENT DOCUMENTS

| | | |
|---|---|---|
| DE | 10 2010 041564 | 3/2012 |
| WO | 2012110082 | 8/2012 |

OTHER PUBLICATIONS

European Patent Office, International Search Report and Written Opinion for PCT/EP2012/071931 dated Sep. 9, 2013,pp. 1-12.
European Patent Office, International Search Report and Written Opinion for PCT/EP2013/072928 dated May 28, 2014,pp. 1-12.

* cited by examiner

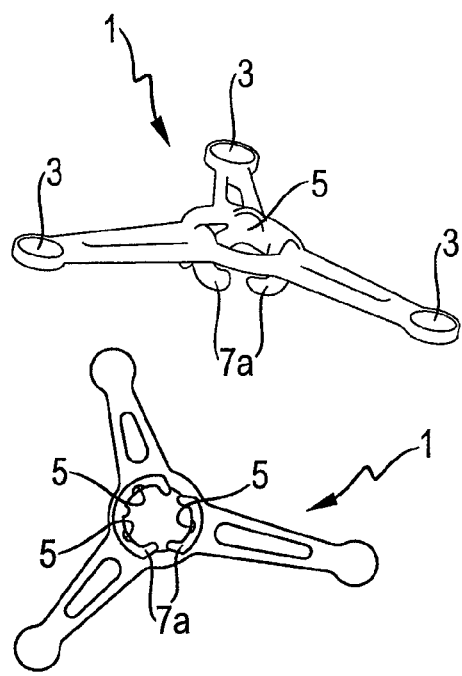
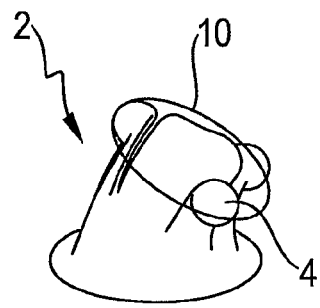
Fig. 8
Fig. 9
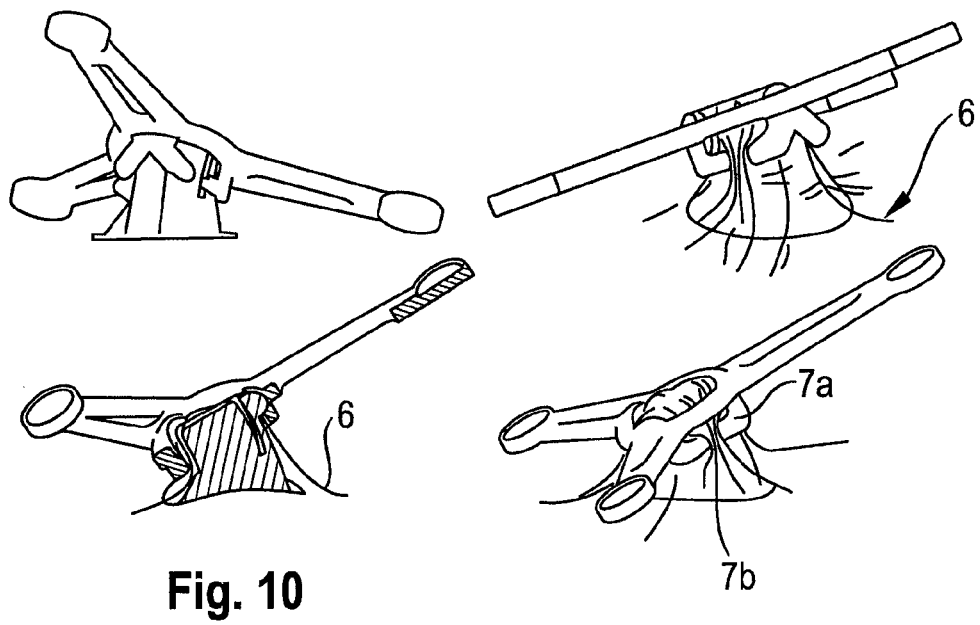
Fig. 10

TWO-PART TRACKING REFERENCE STRUCTURE

RELATED APPLICATION DATA

This application is a national phase application of International Application No. PCT/EP2013/072928 filed Nov. 4, 2013 and published in the English language and which is a continuation-in-part application of International Application No. PCT/EP2012/071931 filed Nov. 6, 2012 and published in the English language.

The present invention relates to a tracking reference structure comprising two connectable parts which allow medical tracking markers to be detachably affixed to an object which is to be tracked within a medical environment. The present invention also relates to a tracking reference system comprising such a tracking reference structure and at least one other support structure for a different type of tracking marker.

Medical tracking markers are known in general, for example from DE 196 39 615 A1, and are used in conjunction with a medical navigation system. It is generally the function of a marker to be detected by a marker detection device (for example, a camera or an ultrasound receiver), such that its spatial position (i.e. its spatial location and/or alignment) can be ascertained. Such markers can be active markers which for example emit electromagnetic radiation and/or waves, wherein said radiation can be in the infrared, visible and/or ultraviolet spectral range. The markers can also however be passive, i.e. can for example reflect electromagnetic radiation from the infrared, visible and/or ultraviolet spectral range. To this end, the marker can be provided with a surface which has corresponding reflective properties. It is also possible for a marker to reflect and/or emit electromagnetic radiation and/or waves in the radio frequency range or at ultrasound wavelengths. Such markers can have a spherical and/or spheroid shape and can therefore be referred to as marker spheres. Such markers can also, however, exhibit a cornered shape, for example a cubic shape, or a disc shape.

WO 2011/038759 A1 discloses a medical tracking marker comprising two parts which can be located on opposite sides of a surgical drape, with the drape placed between them. However, placing a surgical drape between the two parts will inevitably cause a positional shift in the marker(s) relative to the object to be tracked, thereby causing inaccuracies in locating and tracking the object.

PCT/EP2011/052216 discloses a drape-clamping reference array connector comprising two parts which can be connected when they are located on opposite sides of a surgical drape, wherein one part is clamped onto the other part, and a screw is tightened so as to press protrusions of the first part onto a corresponding protrusion of the second part. However, due to the need for several mechanical elements in order to clamp the two parts together, the disclosed structure is rather large and heavy and mounting it is complicated and time-consuming.

It is the object of the present invention to provide a tracking reference structure, for locating and tracking an object by means of a medical tracking system, which overcomes at least one of the above drawbacks, and in particular to provide a tracking reference structure which can be mounted quickly and easily.

The tracking reference structure in accordance with the invention for localising and tracking an object by means of a medical tracking system comprises:

- a first part which forms a support structure for at least one tracking marker; and
- a second part which is configured to be fixed to said object, wherein a positionally fixed connection between the first part and the second part is established by means of an interface comprising at least one resiliently articulated element on the first part and/or second part, which engage(s) with the respective other part, and wherein the resiliently articulated element is configured such that its restoring spring force alone is already sufficient to positionally fix the connection.

In other words, the tracking reference structure in accordance with the invention comprises two separate parts which can be connected via an interface so as to fix, in a positionally determined way, at least one tracking marker to an object which is to be localised and tracked. The tracking reference structure in which the first and second parts are coupled together will maintain the spatial relationship between the marker and the localised and tracked object. One of the first part and the second part can at least partially encompass the respective other part in a plane extending perpendicular to a direction in which the first and second parts are moved relative to each other in order to connect them to each other. If more than one resiliently articulated element is used, these elements are arranged at a greater distance from each other, thus resulting in a higher threshold for moments which may be unintentionally applied to the tracking reference structure, causing the connection between the first and second parts to loosen. Conversely, the interface also allows the first part to be detached from the second part. In order to allow a releasable connection between the first part and the second part, the first and/or second part is connected to at least one resiliently articulated element which engages with the respective other part. The at least one resiliently articulated element is attached to the first or second part in such a way that altering the positional relationship between the element and the part of the tracking reference structure to which the element is attached will generate a restoring spring force which forces the element back to its original position. The interface may be said to allow a so-called "snap-fit" between the first part and the second part. In accordance with the present invention, the connection between the element and the respective part is designed such that the restoring spring force alone is already sufficient to positionally fix the connection between the first and second parts. Consequently, no additional elements for providing a force for the interface are needed other than the at least one resiliently articulated element, in order to positionally fix the first part to the second part while the tracking reference structure is employed in its intended use.

In accordance with a another embodiment of the present invention, the interface is configured so as to allow the first part and the second part to be located on opposite sides of a surgical drape, with the drape placed between the first part and the second part. The tracking reference structure can be used with or without a surgical drape, which is however needed in order to obtain a sterile environment for surgery. As a result, the present invention dispenses with the need for attaching different reference structures to a patient for sterile and non-sterile purposes. If, for example, the object to be localised and tracked is a part of a patient's body such as a patient's head, the second part which is fixed to the patient can be used both before and after the patient has been draped. For registration purposes, a non-sterile marker supporting structure is fixed to the second part, wherein after the patient has been draped, a sterile marker supporting structure is used during surgery. Moreover, as sterility in a surgical environment is of paramount importance, the tracking reference structure is configured such that a surgical drape placed between the first part and the second part is not penetrated, punctured or compromised in any way when the first part and the second part are connected to each other.

The interface may be configured to establish a predetermined spatial position of the first part relative to the second part, irrespective of whether or not a surgical drape is placed between the first part and the second part. Since the position of the tracking markers will not then differ between the draped and undraped state, there is no need to re-register the localised and tracked object in the medical navigation system after a drape has been introduced between the first part and the second part. At least two resiliently articulated elements are for example configured to deflect substantially within the same plane.

Another embodiment of the tracking reference structure in accordance with the invention comprises a positioning aid, wherein the positioning aid comprises means which are specifically formed on the first part and configured to retain drape material, so as to prevent the drape from wrinkling in an area in which a resiliently articulated element engages with the assigned part, and wherein the positioning aid in particular also comprises receiving areas which are specifically formed on the second part and configured to accommodate and retain drape material. Such a positioning aid helps to shorten the time needed in order to connect the first part and the second part and removes the danger of a positional shift caused by a drape wrinkling between the resiliently articulated element and the corresponding part of the tracking reference structure with which the element engages.

Connecting the first part to the second part, with a drape placed between them, is greatly facilitated by a further embodiment of the present invention in which the means which are configured to retain drape material are also configured to automatically tighten the drape in an area in which a resiliently articulated element engages with the assigned part when the first and second parts are connected. The means for automatically tightening the drape could be formed so as to engage the drape when the first part is moved relative to the second part in order to connect the two parts to each other, in such a way that the drape is moved away from the engagement area.

It is also conceivable for the restoring spring force of the at least one resiliently articulated element to be applied to the corresponding other part, i.e. in other words, such that the at least one element is still held by tension when the first part is in its final position and connected to the second part. The tension on the element in this final position of the first part can be smaller than the tension on it during the connecting procedure. Moreover, the force can be applied to the other part either directly or also indirectly via at least one other element.

The positionally fixed connection can be a form-fit connection established by the resiliently articulated element which engages with a correspondingly formed structure of the respective other part and in particular engages into or around said correspondingly formed structure. The first part can for example comprise a male connecting element and the second part can comprise a female connecting element, or vice versa, wherein it is unimportant whether the male and/or female connecting element(s) is/are resiliently articulated.

In accordance with another embodiment, the interface comprises a plurality of discrete contact areas, in particular punctiform, linear and/or laminar contact areas. Three punctiform contact areas or one punctiform and one linear contact area can for example be provided in order to obtain a spatially fixed connection which prevents any relative movement between the first part and the second part of the tracking reference structure. By providing discrete contact areas, it is easier to compensate for small manufacturing tolerances.

It is also conceivable for the first and/or second part to be integrally formed with the resiliently articulated element(s), for example integrally formed from a plastic material, which significantly reduces the manufacturing cost and also the number of components and overall weight of the tracking reference structure. The restoring spring force can thus be provided by the one or more deformed element(s) itself/themselves.

The first part can also be connected to the second part in a translational movement, in particular a combined translational and rotational movement, wherein the direction of the translational movement can also differ from the rotational axis of the rotational movement.

Also, the first part may support at least three tracking markers in order to allow the object to be localised and tracked in three dimensions. The at least three tracking markers can also define a first plane which is tilted relative to a second plane defined by a seat of the second part, which allows the second part to be attached to the localised and tracked object. This configuration can be beneficial in certain O.R. setups in which the distance between the markers as detected by the sensors of the medical tracking system would be too small, and a plane defined by the markers would appear parallel to the surface to which the tracking reference structure is attached.

It should be noted that the second part can be attached to the object/patient using any suitable means, such as for example screws, clamps or adhesive material. Since a number of the features of the tracking reference structure described here enable a lightweight tracking reference structure, adhesive material would also be sufficient to attach the tracking reference structure securely to the object/patient.

In accordance with another embodiment of the present invention, the interface comprises a plurality of resiliently articulated elements which lie on a circle, which can itself lie within the first plane defined by the markers or at least parallel to said plane. Moreover, the resiliently articulated elements can be evenly distributed on said circle.

When the first part is connected to the second part, all the resiliently articulated elements are deflected and can all apply a restoring spring force to the corresponding other part of the tracking reference structure. If the elements are evenly distributed on a circle, this enables the user to choose between several possible positions of the first part relative to the second part when they are connected.

The tracking reference structure can also comprise at least one lever for at least one resiliently articulated element, wherein the lever(s) is/are configured to deflect the element(s), counter to the restoring spring force, and wherein the lever(s) is/are in particular part of a gripping section of the tracking reference structure. As already described above, the second part can be attached to the object/patient via an adhesive connection, such that as little force as possible should be applied to the second part when the first part is connected to it, in order to avoid any possibility of the adhesive connection being loosened. The first part can comprise a gripping section consisting for example of one or more protrusions which are configured to be gripped by a user, wherein the gripping section can comprise one or more of said levers. The one or more elements can be deflected by actuating the one or more levers, such that there is for example no need to press the first part and the second part together in order to cause this deflection. Once the first part has reached its final position with respect to the second part, the user disengages the one or more levers, such that the one or more elements can engage with the corresponding other part of the tracking reference structure.

It is also conceivable for at least one of the one or more levers to comprise a locking mechanism which prevents the lever from deflecting the resiliently articulated element(s), in particular by immobilising the lever relative to the first part of the tracking reference structure. Locking the lever also "locks" the resiliently articulated element(s), such that the first and the second part of the tracking reference structure are securely attached to each other and cannot be detached by unintentionally actuating the secured lever.

The locking mechanism can also comprise an arm which is connected to and extends from the lever, wherein the arm comprises an engaging element which is configured to engage with a corresponding element on the first part of the tracking reference structure. Such an engagement between the engaging element and the corresponding element positionally fixes the arm (and with it, the lever and the resiliently articulated element(s)) to the first part of the tracking reference structure.

It is also conceivable for the engaging element and the corresponding element to releasably engage with each other, in particular in the form of a click-fit or snap-fit connection. Disengaging the engaging element and the corresponding element after the arm, the lever and the resiliently articulated element(s) have been immobilised then causes the deflecting element to be deflectable once again and so allows the first part of the tracking reference structure to be released from the second part of the tracking reference structure once again.

In accordance with another embodiment of the present invention, the tracking reference structure is made entirely of a non-metallic material and/or the first part and the second part can be integrally formed. Such tracking reference structures can be used during EM imaging techniques, wherein a reference structure in which a first part and a second part are integrally formed is light and inexpensive to produce, as already described above.

Another aspect of the present invention relates to a tracking reference system comprising a tracking reference structure as described above which in turn comprises at least one first part, wherein any additional first part(s) support(s) a different type of tracking marker and said different first parts can be interchangeably connected to the second part. The tracking markers of each of said different first parts are preferably placed in the same spatial position when being coupled to the second part, wherein it is also conceivable for the different types of markers to comprise at least one of the following:
  flat optical/reflective markers;
  at least partially spherical optical/reflective markers;
  sterile markers;
  non-sterile markers;
  passive markers;
  active markers;
  MR marker, configured to be used in connection with Magnetic Resonance Imaging (MRI);
  EM markers, configured to be used in connection with an Electromagnetic (EM) Tracking System;
  CT markers, configured to be used in connection with Computer Tomography (CT);
  ultrasound markers.

Such a tracking reference system enables the user to choose, from a plurality of first parts which respectively support different types of markers, the first part comprising markers which best suit a given task, wherein the user can swap the first part as often as desired, without having to re-register the localised and tracked object/patient, since the markers of different first parts will always assume the same spatial position with respect to the patient/object.

In the following, the present invention is described in more detail by referring to particular embodiments and to the attached drawings. It should be noted that each of the features of the present invention, as referred to in this document, can be implemented separately or in any expedient combination.

FIG. 8 shows a first part of a second embodiment of the tracking reference structure.

FIG. 9 shows a second part of another embodiment of the tracking reference structure.

FIG. 10 shows the first part and second part according to the second embodiment of the tracking reference structure in accordance with the invention, connected to each other, both with and without a surgical drape placed between them.

Figure 1:
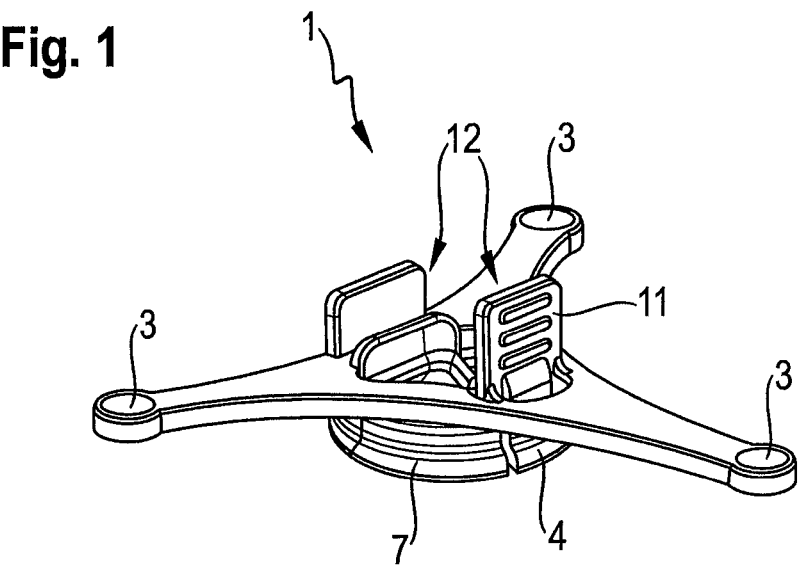
FIG. 1 shows the first part of a first embodiment of the present invention.

The first part 1 as shown in FIG. 1 comprises three arms, which extend in different directions, and flat reflective markers 3 at the end of each arm, thereby defining a plane. The first part 1 also comprises a gripping section 12 featuring two protrusions which extend upwards, wherein one of the protrusions forms a lever 11 which is connected to a resiliently articulated element 4. When the protrusions of the gripping section 12 are pressed towards each other, the lever 11 deflects the resiliently articulated element 4 outwards.

Figure 2:
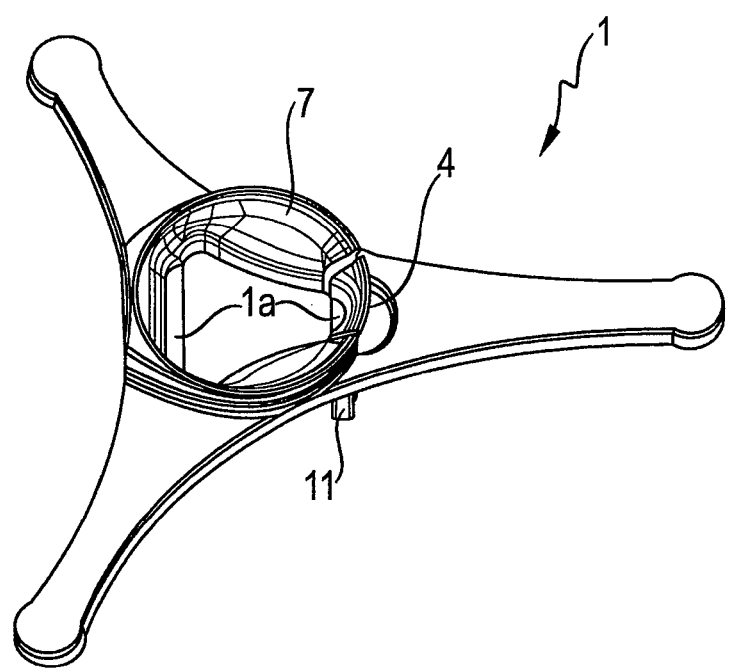
FIG. 2 shows a different view of the first part from FIG. 1.

As can be seen in FIG. 2, deflecting the resiliently articulated element 4 outwards causes discrete contact areas 1a—one formed on the main body of the first part 1, the other formed on the resiliently articulated element 4—to move away from each other, thereby "opening" the interface of the first part 1.

Figure 3B:
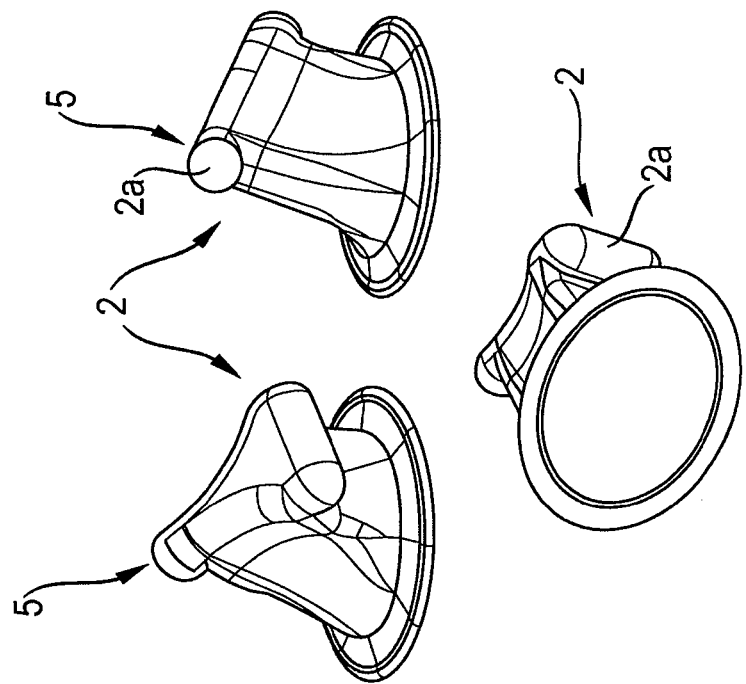
FIG. 3B shows another embodiment of the second part of the first embodiment of the tracking reference structure in accordance with the invention.
Figure 3A:
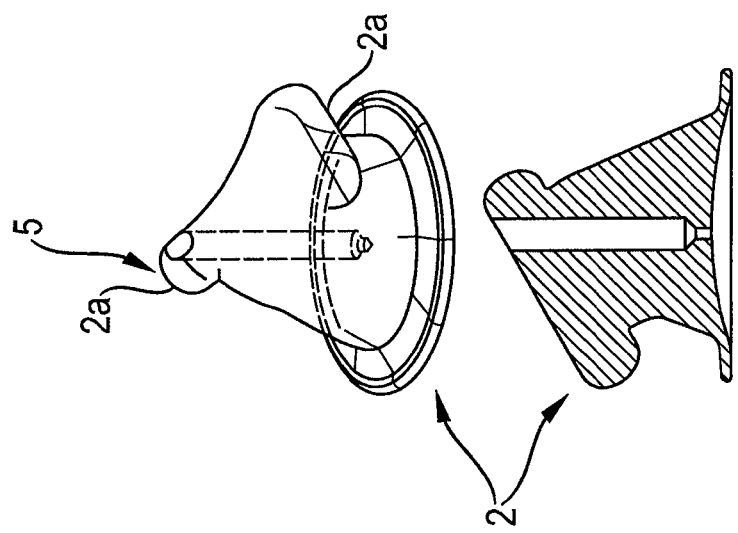
FIG. 3A shows the second part of the first embodiment of the present invention.

FIG. 3A shows a corresponding second part 2 which fits into the receptacle/interface formed in the first part 1, wherein contact areas 2a on the second part 2 contact the contact areas 1a on the first part 1, and wherein the resiliently articulated element 4 encompasses the correspondingly formed structure 5. The second part 2 has a substantially flat, yet slightly curved underside which can be easily attached to a patient's head using adhesive means. Moreover, a central bore (not provided with a reference sign) can be provided so as to allow a screw inserted into the bore to hold down and fix the second part 2 on the patient's skull, as an extra fixation measure beyond adhesive means between the second part and the patient's head.

FIG. 3B shows a number of different views of the second part 2 from FIG. 3A, but with the central bore not indicated.

Figure 4:
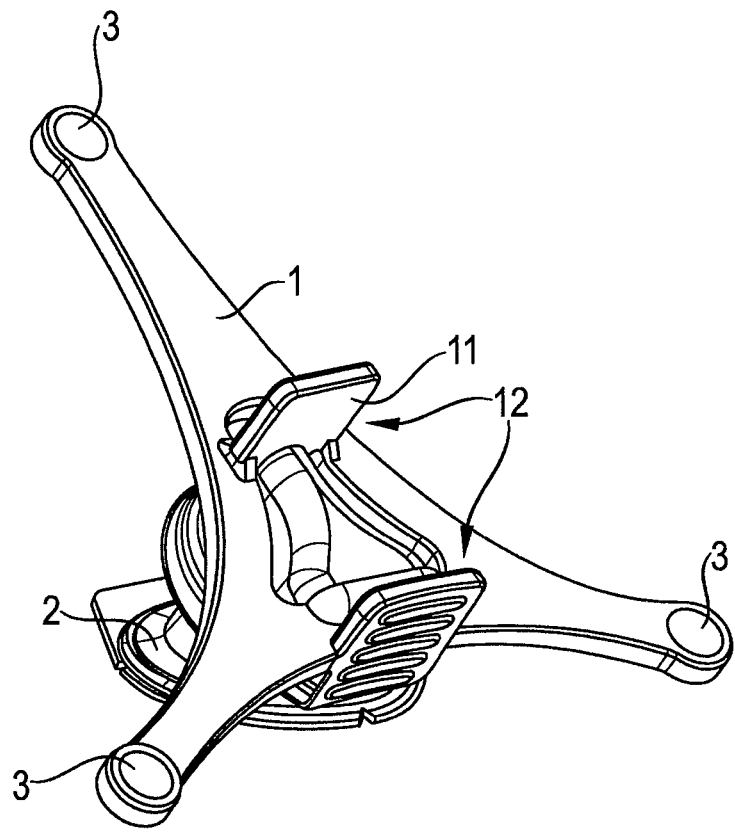
FIG. 4 shows a first part connected to a second part of the first embodiment of the present invention.

FIG. 4 shows the first part 1 connected to the second part 2, wherein a form fit is established by the resiliently articulated element 4 together with the main body of the first part 1. FIGS. 1 to 3 show a circular positioning aid which protrudes from the underside of the first part 1 and aids in positioning the first part 1 on the second part 2 and which also aids in tightening a surgical drape, if one is placed between the first part 1 and the second part 2, in areas in which the contact areas 1*a*, 2*a* contact each other.

As can be gathered from FIGS. 1 to 4, the first part 1 is placed onto the second part 2 in a combined translational and rotational movement, once the lever 11 has been actuated so as to increase the distance between the contact areas 1*a*. Once the first part 1 has been placed onto the second part 2 in a translational movement, it is turned about an axis which is parallel to the linear contact area 1*a* of the first part 1, such that the resiliently articulated element 4 encompasses the correspondingly formed structure 5 once the lever 11 has been disengaged by the user.

Figure 5:
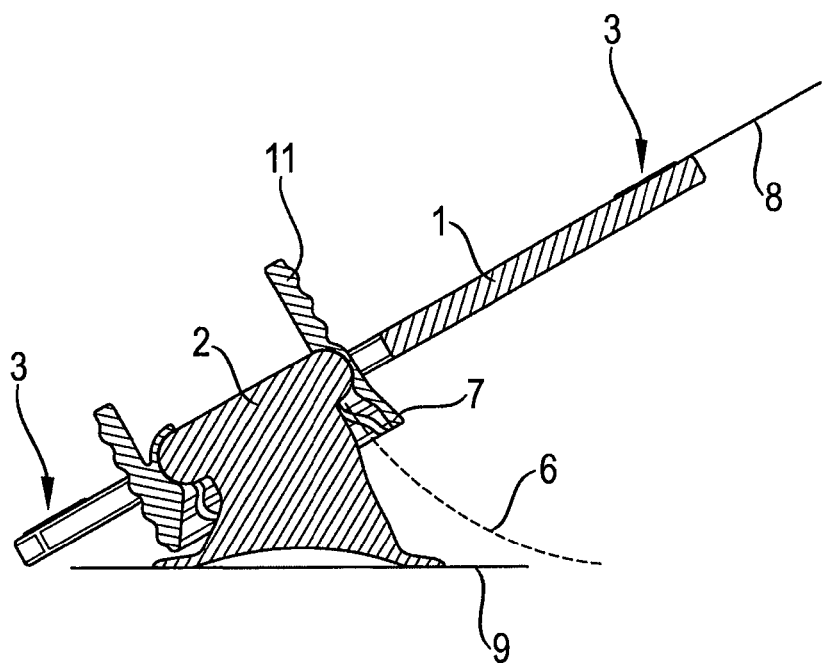
FIG. 5 shows a cross-sectional view of the tracking reference structure from FIG. 4.

FIG. 5 shows a cross-sectional view of the arrangement in FIG. 4, wherein a surgical drape 6 is placed between the first part 1 and the second part 2 and thus extends between the contact areas 1*a* and 2*a*. Since the resiliently articulated element 4 is deflected in a direction which is substantially perpendicular to the tangential plane of the corresponding contact area 1*a*, the position of the first part 1 relative to the second part 2 will not be altered by a surgical drape 6 being placed between them. This kind of deflection can be applied to all the embodiments of the present invention, in order to prevent any positional shift due to the introduction of the surgical drape 6.

FIG. 5 also shows that the plane 8 defined by the markers 3 is tilted with respect to the plane 9 defined by the underside of the second part 2 which is configured to be attached to a patient's head.

Figure 6:
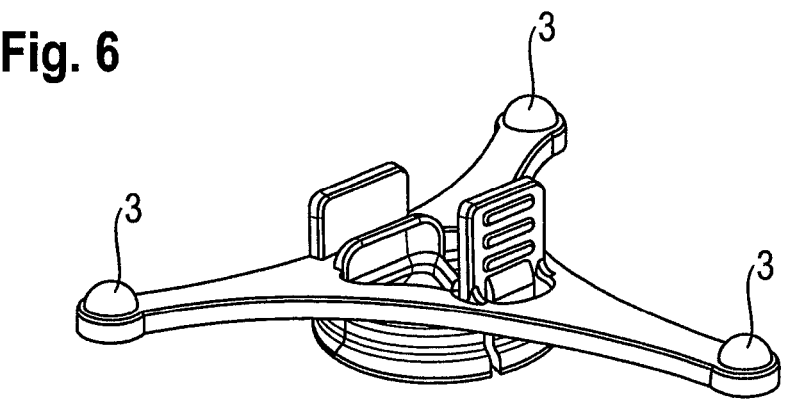
FIG. 6 shows the first part from FIG. 1, supporting another type of marker.
Figure 7:
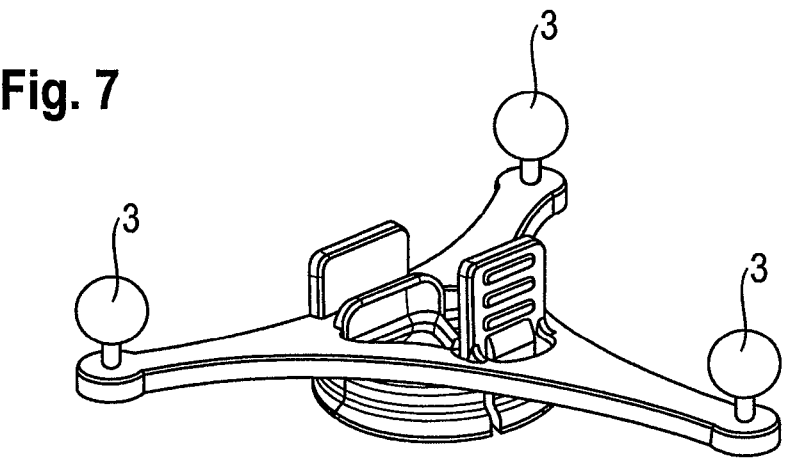
FIG. 7 shows the first part from FIG. 1, supporting yet another type of marker.

FIGS. 6 and 7 show the first part 1 in a configuration already known from FIGS. 1 to 5, but supporting a different type of marker 3. The hemispherical markers shown in FIG. 6 can be MR or CT markers, and the spherical markers 3 shown in FIG. 7 can be spherical reflective markers. All of the first parts 1, irrespective of their different respective types of markers, are formed in such a way that the markers 3 of any given first part 1 will always assume the same position as those of any other first part 1 when the first part 1 is connected to the second part 2, irrespective of the type of marker. This removes the need for re-registration when one first part 1 is replaced with another first part 1.

FIG. 8 shows a first part 1 in accordance with another embodiment of the present invention. The embodiment shown in FIG. 8 comprises flat markers 3, like the embodiment shown in FIG. 1, wherein three discrete and correspondingly formed structures 5 are evenly distributed on an inner surface of the first part 1. In addition, a number of positioning aids in the form of arms extend downwards, adjacent to the correspondingly formed structures 5, and can thus aid in removing folds or wrinkles in the surgical drape between the first part 1 and the second part 2, when the first part 1 is placed on the second part 2.

FIG. 9 shows a second part 2 which fits the first part 1 shown in FIG. 8 and comprises three resiliently articulated elements 4 which are evenly distributed on a circle 10 which is parallel to the plane defined by the markers 3, wherein the plane defined by the circle and the plane defined by the markers are both tilted with respect to the plane defined by the underside of the second part 2.

As can be seen from FIG. 10, receiving areas 7*b* are formed on the second part 2 which accommodate drape material which is then retained by positioning aids 7*a* in areas in which the resiliently articulated elements 4 contact the correspondingly formed structures 5. FIG. 10 also shows, as does FIG. 5, that the second part 2 is circumferentially encompassed by the first part 1, wherein the second part 2 extends into an annular central area of the first part 1.

Figure 11:
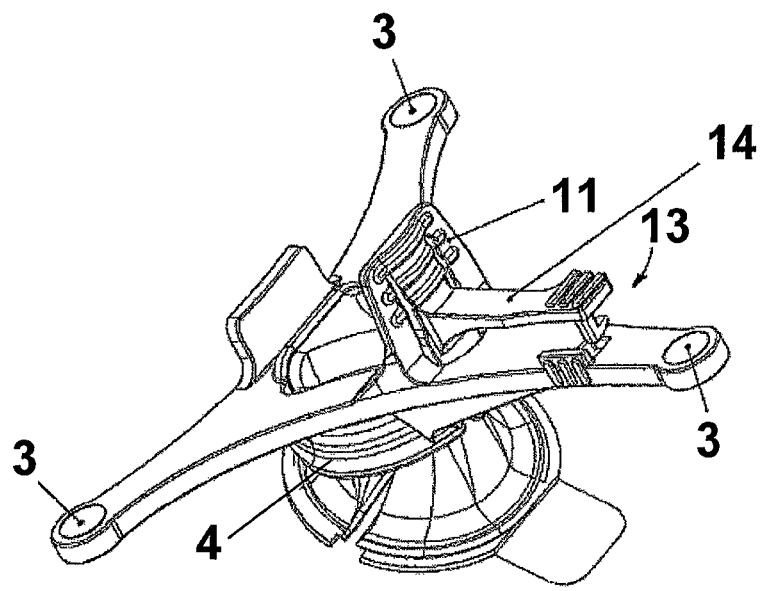
FIG. 11 shows the first part of a third embodiment comprising a lockable lever.
Figure 12:
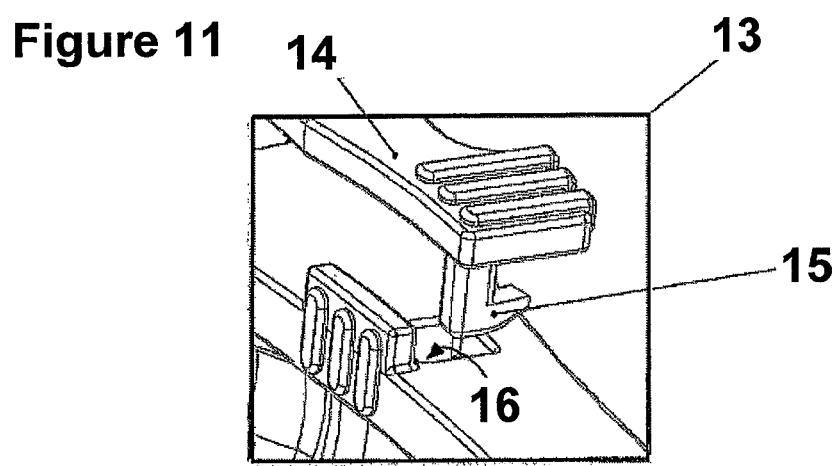
FIG. 12 shows a detailed view of the locking mechanism shown in FIG. 11.

FIG. 11 shows a third embodiment of the tracking reference structure in accordance with the invention, wherein the lever 11, which is configured to deflect the resiliently articulated element 4, comprises an arm 14 which is connected to the lever 11 and extends from it in a direction substantially parallel to a corresponding arm of the first part 1 of the tracking reference structure. The outer end of the arm 14 comprises an engaging element 15 which extends from it and is configured to detachably engage with a corresponding recess 16 which is formed within the first part 1. The engaging element 15 is tapered on one side and has an undercut on the other side, hence the outer end of the arm 14 can be snap-fitted to the first part 1 of the tracking reference structure by pushing the engaging element 15 into the recess 16, thus immobilising the lever 11 relative to the first part 1 such that the lever 11 is prevented from causing any deflection of the resiliently articulated element 4, and the first part 1 is securely attached to the second part 2. Due to the resilient properties of the arm 14, the snap-fit connection can be released by pushing the arm 14 in a direction perpendicular to the direction in which it was pushed in order to be fixed to the first part 1 of the reference structure, such that the rim of the recess 16 moves away from the undercut of the engaging element 15 and the engaging element 15 can move out of the recess 16. The lever 11 is then once again free and able to deflect the resiliently articulated element 4 in order to allow the first part 1 of the reference structure to be placed onto or removed from the second part 2 of the reference structure.

The invention claimed is:

1. A tracking reference structure for localizing and tracking an associated object by a medical tracking system, the tracking reference structure comprising:
   a first part which forms a support structure for at least one tracking marker; and
   a second part which is configured to be fixed to said object;
   wherein a form-fit connection between the first part and the second part is established by a receptacle formed in the first part, wherein the receptacle receives the second part, and wherein the receptacle comprises at least one resiliently articulated element, which engages around a correspondingly formed structure of the second part;
   wherein a restoring spring force forces the resiliently articulated element into a first position where it engages around the correspondingly formed structure; and
   wherein the tracking reference structure further comprises at least one lever for the at least one resiliently articulated element, wherein the lever deflects the resiliently articulated element counter to the restoring spring force and in a direction which is substantially perpendicular to a direction in which the first part and the second part are moved relative to each other in order for the receptacle to receive the second part, and into a second position where the resiliently articulated element does not engage around the correspondingly formed structure.

2. The tracking reference structure according to claim 1, wherein the receptacle allows the first part and the second part to be located on opposite sides of a surgical drape without penetrating the drape when it is positioned between the first part and the second part.

3. The tracking reference structure according to claim 2, wherein the receptacle establishes a predetermined spatial position of the first part relative to the second part, irrespective of whether or not a surgical drape is placed between the first part and the second part.

4. The tracking reference structure according to claim 1, further comprising a positioning aid comprising elements which are specifically formed on the first part to retain drape material, and prevent the drape material from wrinkling in an area in which the at least one resiliently articulated element engages with the second part, and wherein the positioning aid also comprises receiving areas which are specifically formed on the second part and that accommodate and retain the drape material.

5. The tracking reference structure according to claim 4, wherein the elements of the positioning aid are configured to automatically tighten the drape in an area in which the resiliently articulated element engages with the second part when the first part is connected to the second part.

6. The tracking reference structure according to claim 1, wherein the restoring spring force is applied to the second part.

7. The tracking reference structure according to claim 1, wherein the receptacle comprises a plurality of discrete contact areas.

8. The tracking reference structure according to claim 1, wherein the first part is integrally formed with the resiliently articulated element(s).

9. The tracking reference structure according to claim 1, wherein the first part is connected to the second part in a translational movement.

10. The tracking reference structure according to claim 1, wherein the first part supports at least three tracking markers which define a first plane, and the second part comprises a seat which is to be attached to the tracked and localised object and substantially defines a second plane, and wherein the first plane is tilted relative to the second plane.

11. The tracking reference structure according to claim 1, wherein the receptacle comprises a plurality of resiliently articulated elements which lie on a circle which in turn specifically lies within a first plane defined by at least three tracking markers.

12. The tracking reference structure according to claim 1, wherein the at least one lever(s) is/are part of a gripping section of the tracking reference structure.

13. The tracking reference structure according to claim 1, wherein the tracking reference structure is made entirely of a non-metallic material and/or wherein the first part and the second part are integrally formed.

14. The tracking reference structure according to claim 12, wherein at least one of the one or more levers comprises a locking mechanism which prevents the lever from deflecting the element(s) by immobilising the lever relative to the first part.

15. The tracking reference structure according to claim 14, wherein the locking mechanism comprises an arm which extends from the lever and comprises an engaging element which engages with a corresponding element of the first part.

16. The tracking reference structure according to claim 15, wherein the engaging element and the corresponding element engage with each other in a releasable clip-fit or snap-fit connection.

17. A tracking reference system comprising:
a tracking reference structure for localizing and tracking an associated object by a medical tracking system, the tracking reference structure comprising:
at least one first part which forms a support structure for at least one tracking marker;
a second part which is configured to be fixed to said object;
wherein a form-fit connection between the first part and the second part is established by a receptacle formed in the first part, wherein the receptacle receives the second part, and wherein the receptacle comprises at least one resiliently articulated element, which engages around a correspondingly formed structure of the second part;
wherein a restoring spring force forces the resiliently articulated element into a first position where it engages around the correspondingly formed structure;
wherein the tracking reference structure further comprises at least one lever for the at least one resiliently articulated element, wherein the lever deflects the resiliently articulated element counter to the restoring spring force and in a direction which is substantially perpendicular to a direction in which the first part and the second part are moved relative to each other in order for the receptacle to receive the second part, and into a second position where the resiliently articulated element does not engage around the correspondingly formed structure; and
wherein any additional first part(s) support(s) a different type of tracking marker than said at least one tracking marker, and each said additional first part can be interchangeably connected to the second part, and wherein the different type of tracking markers of each of said additional first parts are placed in a same spatial position when being coupled to the second part, and wherein the different types of tracking markers comprise at least one of the following:
flat optical/reflective markers;
at least partially spherical optical/reflective markers;
sterile markers;
non-sterile markers;
passive markers;
active markers;
MR markers;
EM markers;
CT markers;
ultrasound markers.

* * * * *